US006739751B2

(12) United States Patent
Williams

(10) Patent No.: US 6,739,751 B2
(45) Date of Patent: May 25, 2004

(54) X-RAY SYSTEM ALIGNMENT METHOD AND APPARATUS

(75) Inventor: John J. Williams, Hartland, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 72 days.

(21) Appl. No.: 09/681,453

(22) Filed: Apr. 10, 2001

(65) Prior Publication Data
US 2002/0146093 A1 Oct. 10, 2002

(51) Int. Cl.[7] ............................................... A61B 6/08
(52) U.S. Cl. ........................................ 378/205; 378/207
(58) Field of Search ................................. 378/205, 207, 378/162, 163, 164, 19, 98.8, 20

(56) References Cited

U.S. PATENT DOCUMENTS

| 4,064,495 | A | | 12/1977 | Kirkpatrick et al. | |
|---|---|---|---|---|---|
| 5,149,965 | A | * | 9/1992 | Marks | 250/252.1 |
| 5,497,409 | A | | 3/1996 | Jedlitschka et al. | |
| 5,970,119 | A | * | 10/1999 | Hofmann | 378/163 |
| 6,031,892 | A | * | 2/2000 | Karellas | 378/98.3 |
| 6,097,788 | A | | 8/2000 | Berenstein et al. | |
| 6,118,125 | A | | 9/2000 | Carlson et al. | |
| 6,146,489 | A | | 11/2000 | Wirth | |
| 6,379,043 | B1 | * | 4/2002 | Zylka et al. | 378/207 |
| 6,398,408 | B1 | * | 6/2002 | Polkus | 378/207 |

* cited by examiner

Primary Examiner—Craig E. Church
Assistant Examiner—Irakli Kiknadze
(74) Attorney, Agent, or Firm—Artz & Artz, PC

(57) ABSTRACT

An x-ray alignment and measurement process including an x-ray source and a detection array. The detection array allows for the taking of images having a precisely known pixel size and location. Disposed between the x-ray source and the detection array is an object having a known size or position. The object is then imaged and the location and size of the object on the image can be determined and compared to the actual size or location. The calculation is performed on the multiple pixels in the image to mathematically determine the remaining unknown object location or size. For alignment purposes, any error in the location or size of the object can thus be corrected.

27 Claims, 4 Drawing Sheets

X-RAY SYSTEM ALIGNMENT METHOD AND APPARATUS

BACKGROUND OF INVENTION

The present invention relates generally to the mechanical alignment of an x-ray system and, more particularly, to the alignment of an x-ray system and/or the measurement of objects in the field of view through the use of precision image content.

As is known, x-ray systems require precise mechanical alignment of its various components in order to assure proper imaging performance. Specifically, x-ray systems require the mechanical alignment of the x-ray source to a detector, a collimator to the detector, the collimator to the x-ray source and other similar registration of components. In order to ensure proper imaging performance, the various system components must be located a respective predetermined distance and orientation angle from each of the other components. This will provide for images that are to scale and that contain the proper content due to the location of the object to be imaged with respect to the system components.

Current methods for aligning the various components of an x-ray system with respect to one another utilize a ruler or other such device in an attempt to achieve precise measurement. In this process, a test ruler is typically located in the line of sight of the x-ray source and in-between the x-ray source and the detector. Thereafter, an image of the test ruler is taken. Based on the results seen from the image, the size and position of the detector is manually calibrated. This process is repeated until the test ruler is to scale and properly located on the image. While relatively accurate, this process is time consuming and requires significant human intervention, which can introduce alignment errors.

Other prior alignment methods have utilized precise alignment tools to externally position the mechanical components of an x-ray system. These specialized tools have typically been installed on the equipment itself to allow the x-ray team to assist in the alignment process. While these tools provide accurate alignment, they tend to be elaborate and expensive. In addition to alignment purposes, the precise knowledge of position can also be used for a variety of other purposes. These purposes can include, for example, mechanical stability studies, test object measurement, test object alignments, as well as many others. It would thus be advantageous to provide the ability to precisely determine the position of the various components of an x-ray system in a simple, more accurate, cost effective basis.

Moreover, known systems have not had a precise image device. Indeed, these prior systems typically utilize external calibration objects to create a correction matrix for the imager.

SUMMARY OF INVENTION

It is therefore an object of the present invention to provide an x-ray system alignment process that is relatively simple and inexpensive.

It is another object of the present invention to provide x-ray system alignment measurement tools that are relatively simple and inexpensive.

It is yet another object of the present invention to provide an x-ray system alignment process that utilizes measurements from images to ensure proper alignment of the system components.

It is a further object of the present invention to provide an x-ray system that allows for improved object location determination over prior methods.

It is still a further object of the present invention to provide an x-ray system that allows for improved measurement of object size.

In accordance with the above and other objects of the present invention, an x-ray system alignment process is provided. The x-ray system includes an x-ray source and a detection array. The detection array provides for images having a precisely known pixel size. An object of known size and shape is located a predetermined distance between the x-ray source and the detection array. An image of the object is then acquired with the image having a known pixel size. The location of the object on the image can then be determined and an error can be calculated and then corrected through adjustment of the components. It is important that multiple pixels in the image be covered by the shadow of the object. These multiple pixels can then be mathematically evaluated to calculate either a size or position that is a small fraction of the dimension of any one pixel. The process can then be repeated to verify that the mechanical components of the x-ray system are properly aligned. The operator can deduce or calculation can be made on the image from the image what mechanical components to adjust and in which manner to adjust them.

Additionally, the x-ray system may also be utilized to measure external objects and the dynamic performance of the imaging system. An example of such dynamic performance measuring is vibration testing.

Other objects and advantages of the present invention will become apparent upon the following detailed description and appended claims, and upon reference to the accompanying drawings.

BRIEF DESCRIPTION OF DRAWINGS

FIG. 2b is a representation of a view of the derivative of the image of FIG. 2a;

FIG. 2c is a graphic representation of a profile of the pixel values for the enlarged view of FIG. 2a;

DETAILED DESCRIPTION

Figure 1:
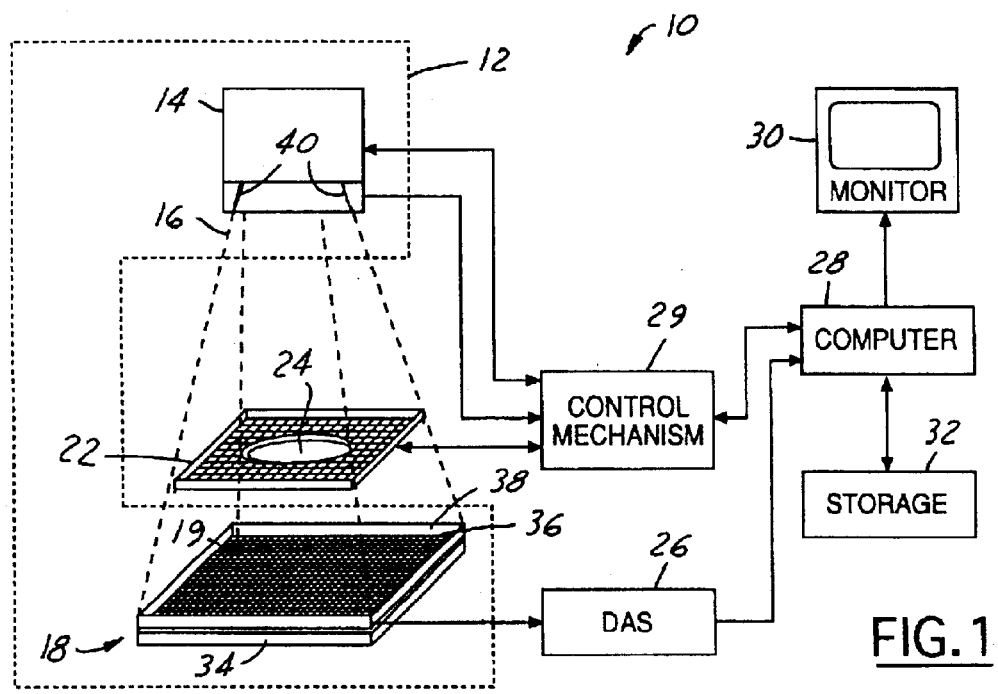
FIG. 1 is a schematic illustration of an x-ray system in accordance with a preferred embodiment of the present invention.

Referring to FIG. 1, an imaging system 10 in accordance with the present invention is shown. The imaging system 10 may be for any type of application, including a vascular x-ray system or a rad x-ray system. However, it will be understood that the system may be utilized in a variety of other applications. The imaging system 10 preferably includes a housing 12 containing an x-ray source 14. The housing 12 may be a gantry having the ability for movement in multiple directions. The x-ray source 14 projects a beam of x-rays 16 towards a detection array 18, which may also be contained within the housing 12. Although not necessary, a collimator 20, connected to the x-ray source, having a plurality of collimator blades 40 may be used to limit the beam of x-rays 16. Positioned in between the x-ray source 14 and the detection array 18 is a table 22, preferably not within housing 12, for holding an object 24 to be imaged by the imaging system 10. A data acquisition system (DAS) 26 registers signals from the detection array 18 and sends the information to a computer 28 for processing. A control mechanism 29 may be used to control the movement and position of the system components as well as power and timing signals to the x-ray source 14. Finally, the imaging system 10 may also include a monitor 30 and storage 32 device for viewing and storing information. While electronic and control mechanism are illustrated, they are not required to perform the calibration and measurement techniques described herein and are merely being shown for illustration purposes only.

Although such a system describes generically an imaging system, the present invention utilizes a high-resolution imager. The imager has a pixel location and dimension of a high order of magnitude precision. Thus, each image will have multiple pixels in the image that will be covered by the shadow of the object. These multiple pixels can then be mathematically evaluated to calculate either a size or position that has a degree of precision that is a small fraction of the dimension of any one pixel. The precision of the imaging device is preferably on the order of 1 micron and this precision can be used to calculate the other dimensions of the system or objects under study. Additionally, for example, the imager may have 200 micron pixels that can be used to measure with an uncertainty of less than 20 microns. It should be understood that additional orders of magnitude precision may also be utilized. High-resolution imagers are well known in the prior art. The detection array 18, on such high-resolution systems, includes a plurality of pixel panels 19. Although a variety of pixel panel 19 shapes, sizes and densities are contemplated, in one embodiment the detection array 18 includes 1000×1000 pixel panels 19 that are shaped as 200 micron sided squares. In addition, it is required that variations in pixel size and location be minimized. In one embodiment, the uncertainty in pixel size and location is less than 10 microns. A variety of detection arrays 18 includes a glass substrate 34, a photodetector array 36 and a scintillator 38. In other embodiments, however, alternative detection array 18 configurations are contemplated.

As is known, the x-ray system 10 requires the mechanical alignment of the x-ray source 14 to the detection array 18, the collimator 20 to the detection array 18, the collimator 20 to the x-ray source 14, and other similar registration of components to assure proper imaging performance. The alignment process typically occurs during installation of the system, but can also occur periodically to ensure proper performance. In accordance with the present invention, it has been discovered that the availability of high-resolution digital images with precise pixel location makes possible the accurate alignment of the system components through calculations from images taken in defined conditions. In accordance with the present invention, the detection array 18 can precisely define image pixels that are 200 microns square. Such a precise detection array can be readily obtained. Image pixels of this known size provide samples of the image at well known locations that can be used to measure distances and locations in the image with great accuracy. In accordance with the preferred embodiment, these measurements can be made with minimal uncertainty and can be used for multiple practical applications.

Given that the pixel size provides precise x-ray images, an image of an attenuating object which is larger than the imager pixel size has a large number of pixels that are partially covered (fiducial object) around the edge of the object. Based on the pre-existing knowledge of the shape of the object, a best fit to the shape can be determined. If the object is an edge, a sphere or other known shape, its shape or footprint can be determined. The best fit of the shape can attain spatial resolutions that are substantially finer than the pixel size. It has been determined that measurements of the shape can then be made with an uncertainty of less than 20 microns.

The resulting measurements as to the location of the object can then be used as a tool to control system geometry or measure system performance. For example, if an object is located at an intermediate position between the detection array 18 and the x-ray source 14, any change in the relative position of any of the x-ray source 14, the detection array 18, or the object, will be observed in the image position on the detection array 18, because the collimator 20 is an object in this image view. The alignment of the collimator 20 to an image field can be evaluated by imaging the location of the collimator shadow. As is known, the image of the collimator blades 40 has a gradual edge due to the large distance between the collimator 20 and the detection array 18. However, by using an appropriate differentiation and threshold to fit to this edge image, it is practical to determine the location of the edge of the collimator blades 40 to sub-millimeter precision. This location measurement can be used either for alignment of the collimators and/or verification of collimator position change with time, housing position, or FOV tracking.

During use, the x-ray source 14 may become relatively displaced with respect to the detection array 18. The amount of this displacement can be determined in accordance with the preferred embodiment, by placing fiducial objects in the path of the x-ray source 14 and observing the amount of image shift as the position of the housing 12 is changed. For example, as shown in FIGS. 2 through 5, an object such as a ball bearing can be taped or otherwise adhered to the exit window of the x-ray tube. Alternatively, the ball bearing can be secured to the scatter grid, the collision sensor, or to any other intermediary structure. The position of the ball bearing can then be measured through the range of motion of the x-ray system components. This displacement can be quantified either in a static location, or dynamically, as the motion is occurring.

Alternatively, the alignment of the x-ray source 14 to the detection array 18 can be triangulated by imaging fiducial objects in more than one plane. By calculating the relative location of the objects, it is possible to determine the direction, centering and distance of the x-ray source 14. The motion alignment of the housing 12 can be either calibrated or verified using the above method of triangulation. The parallel motion of the detection array 18 or the x-ray source 14 can be determined by taking multiple measurements over the range of travel. This will determine both the straightness of the travel as well as any deviation from the expected deviation of motion.

FIGS. 2, 2a, 2b, 2c and 2d illustrate an exemplary image for use in connection with the disclosed alignment method. The image shown in FIG. 2 has four collimator blades 54 that define an illuminated image area therebetween, which is generally indicated by reference number 60. The collimator blades each define a respective edge 62, 64, 66 and 68. The illuminated area 60 includes three spheres 70, 72, 74, located very near the detection array 18 and another sphere 76 located near the x-ray source 14. Both the collimator blades 54 and the sphere 76 are mechanically mounted to the x-ray source 14. In this example, the spheres 70, 72, 74 are the same size as the sphere 76 and in this case are 2 mm diameter steel ball bearings. They appear to be different sizes in the Figures because they are not at the same relative distance from the x-ray source 14 to the detection array 18. However, it should be understood that objects of varying sizes and shapes may be utilized, so long as their size and shape is known. While the spheres 70, 72, 74 and 76 are preferably ball bearings, other objects may be utilized.

Figure 2:
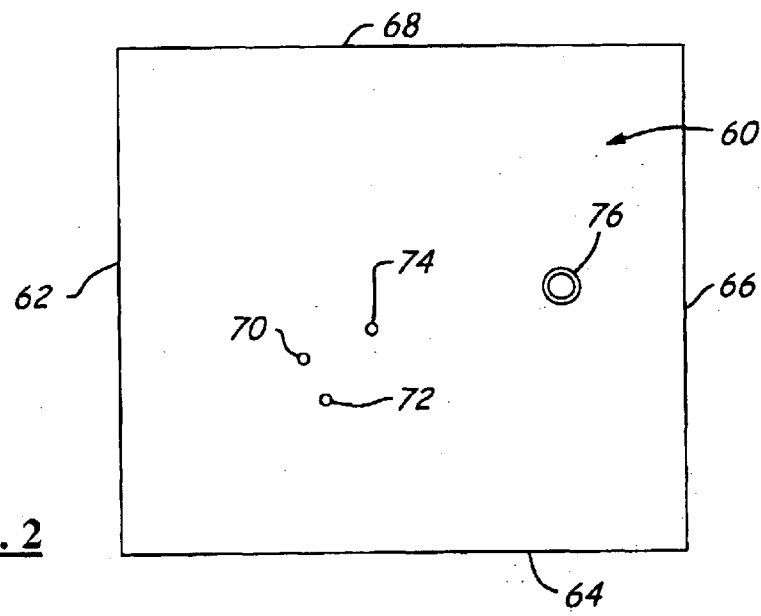
FIG. 2 is a representation of an image of three objects located near a detection array and one object located near an x-ray source in accordance with a preferred embodiment of the present invention.
Figure 2A:
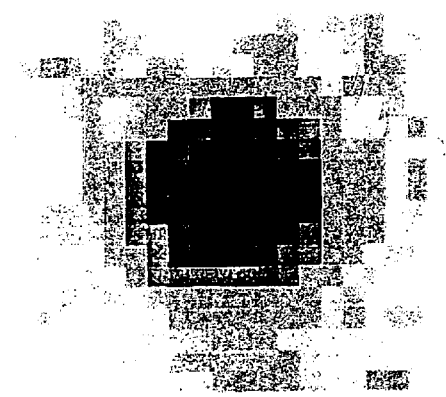
FIG. 2a is a representation of an enlarged view of one of the objects located near the detection array shown in FIG. 2.
Figure 2B:
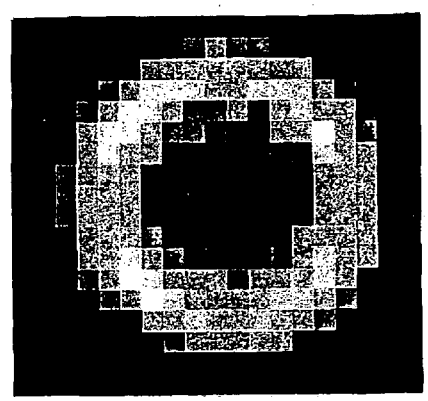
Figure 2C:
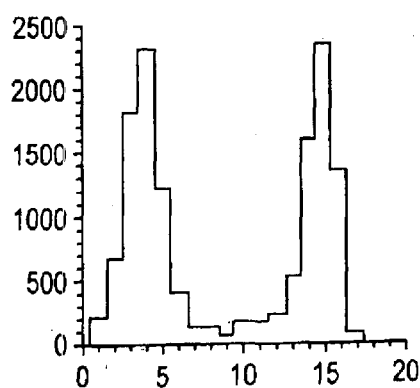
Figure 2D:
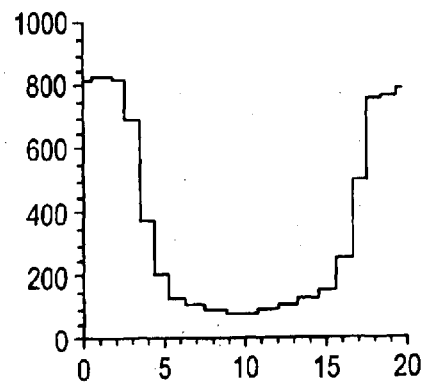
FIG. 2d is a graphic representation of a profile of the pixel values for the derivative of the image of FIG. 2b.

FIG. 2*a* is an enlargement of a portion of the illuminated area 60, and specifically of the sphere 70. This image illustrates that the image is composed of a plurality of finite sized pixels, with the pixels being smaller than the size of the spheres 70, 72, 74 and 76. As shown, the image of the sphere 70 has an edge or periphery that is sampled at a substantial number of locations. As also seen, the edge is not determined or defined at a precise location. In accordance with the preferred method, the derivative of the image of FIG. 2*a* is taken, which gives a sampling of locations for the object edge that is independent of image brightness and contrast because the location of maximum change will always be the maximum derivative location. The derivative of the image is shown in FIG. 2*b*. Profiles of the pixel values for the image and the image derivative are shown respectively in FIGS. 2*c* and 2*d*. These profiles assist in determining the location of the edge more precisely.

Figure 3:
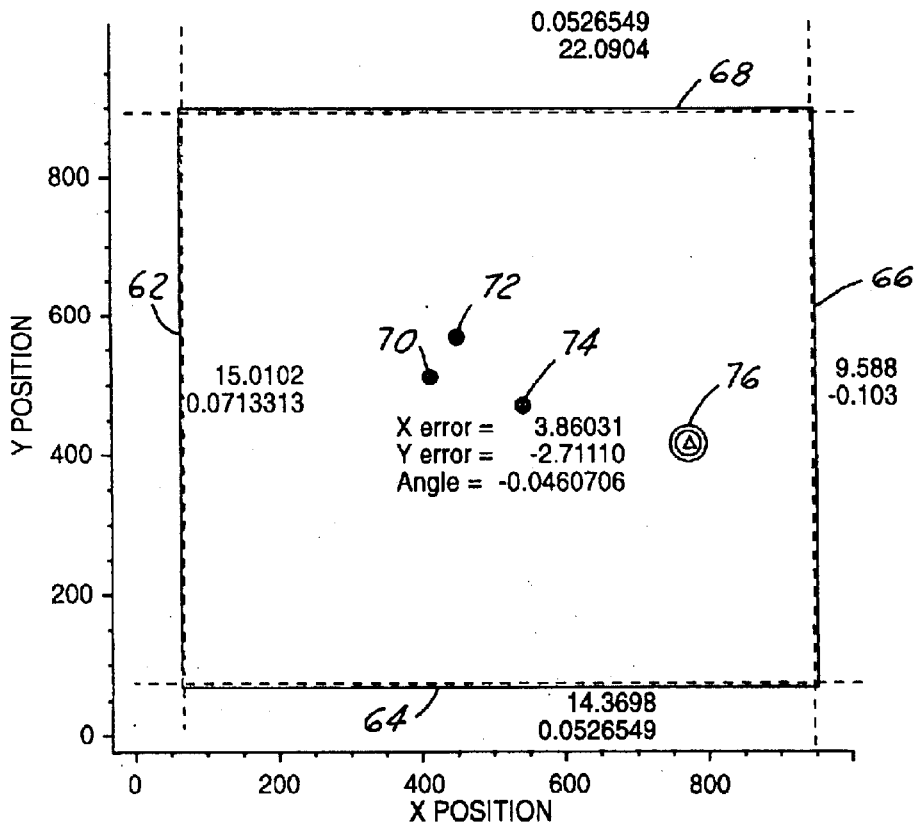
FIG. 3 is a graphic representation of the location of one of the objects in an x-ray coordinate frame.

In accordance with the preferred method disclosed above, the sample images may be evaluated to determine a typical response. From these calculations a best fit linear equation for each of the objects 70, 72, 74, 76 to each of the edges of the collimator blades 62, 64, 66 and 68 and an X, Y and angle error calculated from each of those edges can then be determined. In the disclosed example, the sample images shown in FIGS. 2 and 2*a* –2*d* were evaluated to determine the best fit linear equation. The determined response is illustrated in FIG. 3. In accordance with the calculations, the collimator edge 62 is located 15.0102 mm in the x-ray direction from the center pixel the image with an angle error of 0.0713313. The collimator edge 64 is located 14.3698 mm in the y-direction from the center of the image with an angle error of 0.0526549. The collimator edge 66 is located 9.588 mm in the x-direction from the center pixel of the image with an angle error of 0.103. The collimator edge 68 is located 22.0904 mm in the y-direction from the center pixel of the image with an angle error of 0.0526549. The collimator 20 was determined to have an x-error of 3.86031, a y-error of 2.71110, and an angle error of 0.0460706 with respect to its actual known position. Based on this knowledge, the components of the system can be adjusted accordingly to eliminate the error.

Figure 4:
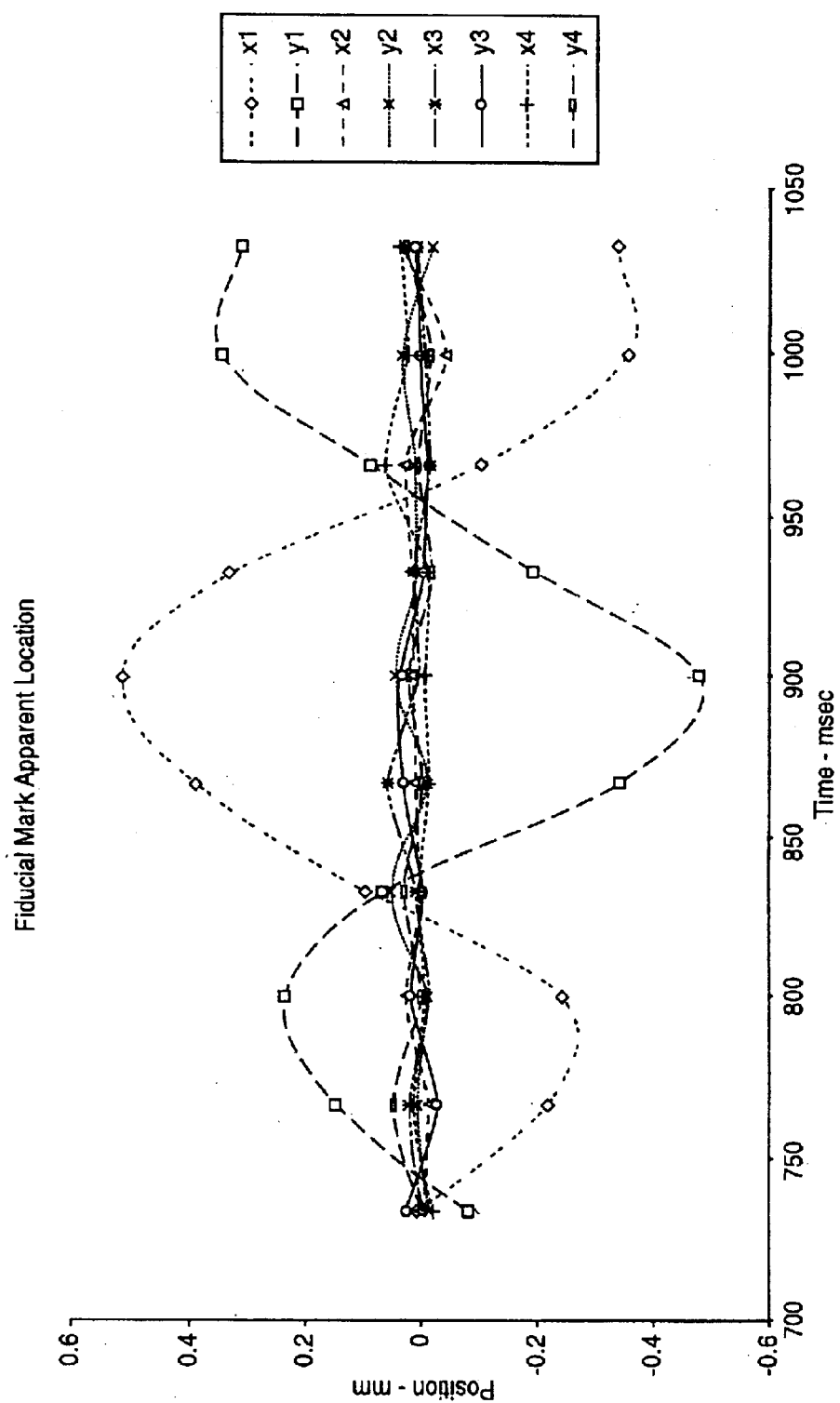
FIG. 4 is a graphic representation of the location of the objects in the image of FIG. 2 measured over several frames in accordance with a preferred embodiment of the present invention.

The locations of the objects in the images above are preferably measured over several frames for dynamic position evaluation. For static position evaluation, and if multiple images are obtained, then the images can be summed to minimize image noise effects. However, their respective locations can also be measured based on a single frame. FIG. 4 illustrates a graph of the apparent position of each of the spheres over a given period of time. The apparent position was determined based on images taken over the given period of time. As shown, the object 76 was moving in a periodic form as might be expected from the non-rigid nature of the x-ray tube support structure. Conversely, the three spheres 70, 72, 74, which were attached directly to the detection array 18, show much smaller variation. It is assumed that all the variation is coming from measurement uncertainty, and thus the small objects 70, 72, 74 have a variation of only 0.02 mm standard deviation. This variation is 1/10 of the size of the image pixel. Thus, the calculations from the images are highly precise with only minimal uncertainty.

Figure 5:
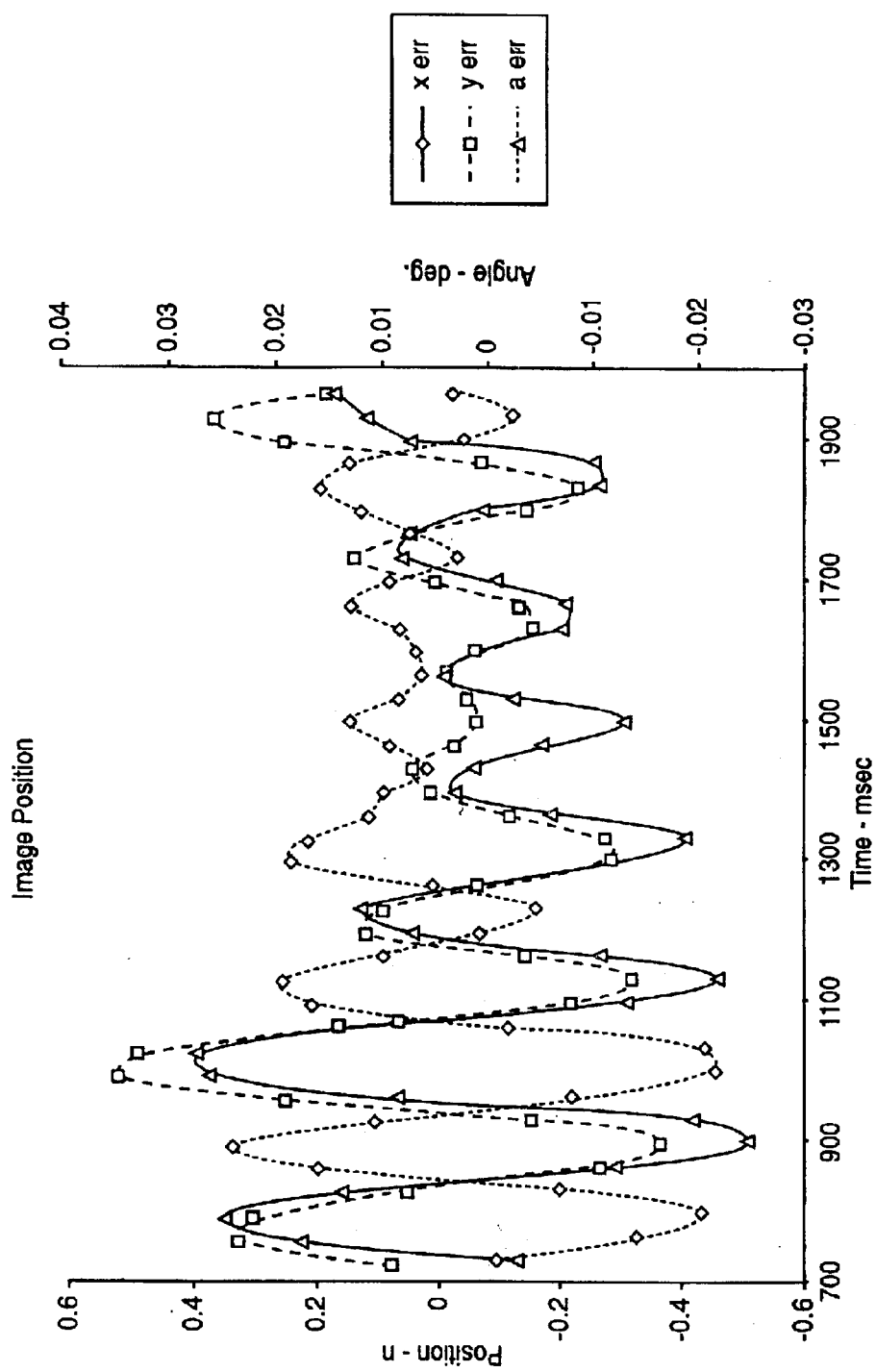
FIG. 5 is a graphic representation of the observed location of the collimator blades over the same series of image frames as measured in FIG. 4.

FIG. 5 is a graph illustrating the observed location of the collimator blades 62, 64, 66 and 68 over the same period of time measured above, as determined from multiple image frames. It can thus be seen that the location of the collimator blades 62, 64, 66, 68 are changing by far more than the uncertainty in the measurements. The disclosed method thus provides the ability to make high precision measures of the location of components in the x-ray image chain by taking advantage of the precision location sampling of the detection array 18. Only minimal accuracy requirements are placed on external tools.

In accordance with the preferred embodiment, the location determination is much better than the pixel size. Further, the location is determined by an average of multiple samples. Moreover, the measurement precision is not tied to the object precision. This is in part because the locations are determined by centroids of the objects rather than by absolute measurement. Additionally, self-alignment of the system components can be made by acquisition of a test image, calculation of error, and application of the error correction adjustment. Further, the preferred method provides time dependent measurements by the use of multiple image samples at normal system frame rates of 30 frames per second (fps) or whatever the system provides.

While the disclosed example aligns the system components based on the location of the object 70 that is attached to the detection array 18, the location of objects in other planes, such as the object 76, attached to the x-ray source 14 can be utilized to align the system components. Moreover, multiple objects can also be utilized to align the system components. Additionally, the use of relative sizes and locations can be used for most applications. For example, the distance from the x-ray source 14 to the detection array 18 may be observed by measuring the relative image size of two same sized objects with a known difference in distance from an image plane. Ratios can be used to calculate the distances involved. As will be understood, field applications are applicable to all modalities.

While the invention has been described in connection with one or more embodiments, it should be understood that the invention is not limited to those embodiments. On the contrary, the invention is intended to cover all alternatives, modifications, and equivalents, as may be included within the spirit and scope of the appended claims.

What is claimed is:

1. A method for aligning the components of an x-ray system, having an x-ray source and a detection array capable of generating images having a known pixel size, comprising:

locating an object of known size and shape at a predetermined distance between the x-ray source and the detection array;

acquiring an image of said object; and determining a location and size of said object on said image; and comparing said measured location and size of said object to said known size and location.

2. The method of claim 1, further comprising:

acquiring multiple images of said object; and determining said location and size of said object based on said multiple images.

3. The method of claim 2, wherein said object is secured to the detection array.

4. The method of claim 2, wherein said object is secured to said x-ray source.

5. The method of claim 2, wherein said object is secured to the detection array and another object is secured to the x-ray source.

6. The method of claim 1, further comprising:

connecting said x-ray source to a collimator having a plurality of collimator blades;

determining a best fit linear equation from said object to each of the plurality of collimator blades.

7. The method of claim 1, further comprising:
taking a derivative of said image to more precisely define the periphery of said object.

8. A method for aligning the components of an x-ray system comprising:
providing an x-ray source emitting an x-ray beam;
locating a detection array remotely from said x-ray source;
disposing an object of known size and shape in a first plane, said plane being located a known distance from one of said x-ray source or said detection array;
acquiring at least one image of said object, said at least one image having a known pixel value;
determining a location and size of said object from said acquired image; and
compensating for any differences between said known size and shape of said object and said determined size and location.

9. The method of claim 8, further comprising:
locating a plurality of collimator blades adjacent said x-ray source to create an illuminated area into which said object is disposed.

10. The method of claim 9, further comprising:
taking a derivative of said at least one image to provide a sampling of locations for said object periphery.

11. The method of claim 10, further comprising:
profiling pixel values of said at least one image and said derivative of said at least one image.

12. The method of claim 9, further comprising:
acquiring multiple images of said object.

13. The method of claim 12, further comprising:
determining a best fit linear equation to each of said plurality of collimator blades; and
calculating any x, y and angle error from said object to each of said plurality of collimator blades.

14. The method of claim 9, further comprising:
locating a second object in a second plane.

15. The method of claim 14, further comprising:
imaging said second object.

16. The method of claim 15, further comprising:
calculating the relative location of each of said first and second objects so as to determine the direction, centering and distance of said x-ray source.

17. A method for x-ray system alignment using precision image content, comprising:
locating an x-ray source with respect to a detection array, said detection array having known precisely defined image pixels;
disposing an object of known size and shape between said x-ray source and said detection array, said object being larger than the images pixel size;
attenuating said object with respect to said x-ray source or said detection array;
taking at least one image of said object; and
computing a best fit to the shape of said object based on said known size and shape.

18. The method of claim 17, wherein said best fit has spatial resolutions that are substantially finer than said image pixel size.

19. The method of claim 18, further comprising:
taking multiple images of said object; and
determining whether there is any change in the position of said image, indicating a change in the relative position of said x-ray source, said detection array or said object.

20. The method of claim 19, further comprising:
mounting a plurality of collimator blades to said x-ray source such that a collimator shadow is found; and
imaging the location of said collimator shadow.

21. The method of claim 20, further comprising:
determining the location of said collimator shadow; and
aligning said collimators based on said determined location.

22. The method of claim 18, further comprising:
observing any image shift in said object; and
calculating any relative displacement of said x-ray source to said detection array.

23. A method for determining the measurement of an external object, comprising:
providing an x-ray system having a source and a detection array;
providing said detection array with image pixels of a predefined size and position;
locating the object which is of known shape and known size or location in a field of view of said source, said object being larger than said predefined size of said image pixels;
acquiring an image of said object;
computing a best fit shape of said object based on pre-existing knowledge of said object; and
determining the other of said size or location of said object.

24. The method of claim 23 further comprising:
sampling an edge of said object at a plurality of locations.

25. The method of claim 24 further comprising:
taking a derivative of said image to acquire a sampling of locations for said edge of said object that is independent of image brightness and contrast.

26. A method for performing dynamic or stability testing of an x-ray system including an x-ray source and a detection array comprising:
fixing an object of known size and shape to a position of the x-ray system in a field of view of the x-ray source;
acquiring multiple images of said object over a predetermined period of time; and
monitoring said object position as a function of time.

27. The method of claim 26 further comprising:
determining whether any components of the system has moved over time based on said acquired multiple images.

* * * * *